US00PP29404P2

(12) United States Plant Patent
Barbour

(10) Patent No.: US PP29,404 P2
(45) Date of Patent: Jun. 19, 2018

(54) ***THUJA* TREE NAMED 'ATTAPULGUS'**

(50) Latin Name: *Thuja standishii×Thuja plicata*
Varietal Denomination: Attapulgus

(71) Applicant: John Barbour, Hawkinsville, GA (US)

(72) Inventor: John Barbour, Hawkinsville, GA (US)

(73) Assignee: Athena Trees, Inc., Hawkinsville, GA (US)

( * ) Notice: Subject to any disclaimer, the term of this patent is extended or adjusted under 35 U.S.C. 154(b) by 0 days. days.

(21) Appl. No.: 15/731,110

(22) Filed: Apr. 19, 2017

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

*Primary Examiner* — Kent L Bell
(74) *Attorney, Agent, or Firm* — C. A. Whealy

(57) ABSTRACT

A new and distinct cultivar of *Thuja* tree named 'Attapulgus', characterized by its upright and narrowly conical tree form; vigorous growth habit and rapid growth rate; freely and upswept branching habit; dense and bushy form from base to top of the tree; dark green-colored leaves; and leaves resist "yellowing" and maintain green coloration during the winter.

4 Drawing Sheets

Botanical designation: *Thuja standishii×Thuja plicata.*
Cultivar denomination: 'ATTAPULGUS'.

BACKGROUND OF THE INVENTION

The present invention relates to a new and distinct cultivar of *Thuja* tree, botanically known as *Thuja standishii×Thuja plicata*, commonly known as Western Arborvitae and hereinafter referred to by the name 'Attapulgus'.

The new *Thuja* tree is a naturally-occurring whole tree mutation of *Thuja standishii×Thuja plicata* 'Green Giant', not patented. The new *Thuja* tree was discovered and selected in 2010 by the Inventor as a single tree from within a population of trees of 'Green Giant' planted in 2006 in an outdoor nursery environment in Hawkinsville, Ga.

Asexual reproduction of the new *Thuja* tree by hardwood cuttings in a controlled environment in Bishop, Ga. since January, 2012, has shown that the unique features of this new *Thuja* tree are stable and reproduced true to type in successive generations.

SUMMARY OF THE INVENTION

Trees of the new *Thuja* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Attapulgus'. These characteristics in combination distinguish 'Attapulgus' as a new and distinct *Thuja* tree:

1. Upright and narrowly conical tree form.
2. Vigorous growth habit and rapid growth rate.
3. Freely and upswept branching habit; dense and bushy form from base to top of the tree.

4. Dark green-colored leaves; leaves resist "yellowing" during the winter and maintain green coloration in USDA Hardiness Zone 8.

Trees of the new *Thuja* can be compared to trees of the mutation parent, 'Green Giant'. Trees of the new *Thuja* differ primarily from trees of 'Green Giant' in the following characteristics:

1. Trees of the new *Thuja* are more narrowly conical than trees of 'Green Giant'.
2. Trees of the new *Thuja* are more freely branching and are denser and fuller than trees of 'Green Giant' especially towards the apex of the tree.
3. Trees of the new *Thuja* have a more narrowly upswept branching habit than trees of 'Green Giant'.
4. Trees of the new *Thuja* have shorter internodes than trees of 'Green Giant'.
5. Trees of the new *Thuja* have darker green-colored leaves than trees of 'Green Giant'.
6. Leaves of trees of the new *Thuja* resist "yellowing" during the winter whereas leaves of trees of 'Green Giant' become yellow green in color during the winter.

Trees of the new *Thuja* can be compared to trees of *Thuja standishii×Thuja plicata*, 'Steeplechase', disclosed in U.S. Plant Pat. No. 16,094. In side-by-side comparisons, trees of the new *Thuja* differ primarily from trees of 'Steeplechase' in the following characteristics:

1. Trees of the new *Thuja* are more narrowly conical than trees of 'Steeplechase'.
2. Trees of the new *Thuja* are faster-growing than trees of 'Steeplechase'.
3. Trees of the new *Thuja* have a more upswept branching habit than trees of 'Steeplechase'.

BRIEF DESCRIPTION OF THE PHOTOGRAPHS

The accompanying colored photographs illustrate the overall appearance of the new *Thuja* tree showing the colors as true as it is reasonably possible to obtain in colored reproductions of this type. Colors in the photographs may differ slightly from the color values cited in the detailed botanical description which accurately describe the colors of the new *Thuja* tree.

The photographs on the first sheet are side perspective views of typical ten-year trees of 'Attapulgus' (left) and 'Green Giant' (right) grown during the summer showing the differences in overall tree shape.

The photographs on the second sheet are close-up views of the upper sections of typical ten-year trees of 'Attapulgus' (left) and 'Green Giant' (right) grown during the summer showing the differences in branching habit and branching angle.

The photographs on the third sheet are close-up views of typical ten-year trees of 'Attapulgus' (left) and 'Green Giant' (right) grown during the winter showing the "yellowing" on the leaves of 'Green Giant' and the absence of "yellowing" on the leaves of 'Attapulgus'.

The photographs on the fourth sheet are close-up views of the main stem and lateral branches of typical ten-year trees of 'Attapulgus' (left) and 'Green Giant' (right) grown during the summer showing the differences in branching angle.

DETAILED BOTANICAL DESCRIPTION

The aforementioned photographs and following observations, measurements and values describe trees grown during the summer and winter in ground beds in an outdoor nursery in Hawkinsville, Ga. and under cultural practices typical of commercial *Thuja* tree production. During the production of the trees, day temperatures averaged 24.5° C. and night temperatures averaged 11.1° C. Trees used in the photographs and for the description were ten years old. In the following detailed description, color references are made to The Royal Horticultural Society Colour Chart, 2007 Edition, except where general terms of ordinary dictionary significance are used.

Botanical classification: *Thuja standishii*×*Thuja plicata* 'Attapulgus'.

Parentage: Naturally-occurring whole tree mutation of *Thuja standishii*×*Thuja plicata* 'Green Giant', not patented.

Propagation:

*Type*.—By hardwood cuttings.

*Time to produce rooted young trees, winter*.—About 20 days at temperatures about 21° C.

*Root description*.—Medium in thickness.

*Rooting habit*.—Moderately freely branching; medium density.

*Root color*.—Developing roots, close to between 158A to 158B and 162C; developed roots, close to between 173B and 175B.

Tree description:

*Tree and growth habit*.—Woody ornamental evergreen tree; upright and narrowly conical tree form; vigorous growth habit; rapid growth rate, trees grow about 67 cm in height per year.

*Tree height*.—About 6.7 meters.

*Tree diameter, base*.—About 3.05 meters.

*Trunk caliper, base*.—About 25.4 cm.

*Height to width ratio*.—About 2.2:1.

*Branching habit*.—Freely and upswept branching habit; branch angle ranges from about 37.5° (proximally) to 24° (distally); about 92 primary lateral branches per tree with numerous secondary and tertiary branches; dense and bushy habit from base to top of tree.

*Lateral branch description*.—Length: About 1.6 meters. Diameter: About 3.2 cm. Internode length: About 7 cm. Strength: Strong, flexible. Texture, developing branches: Somewhat scaly becoming more smooth and glabrous with development. Texture, trunk: Scaly vertical strips; underneath outer bark, smooth and glabrous. Color, developing branches: Close to 145A with spots, close to 164A; distally, close to between 164A and 165A. Color, developed branches: Close to between 198A to 198B and 195A; underneath, close to N187B. Color, trunk: Patches of close to 201B and 202D; color becoming closer to 198A and 198B with development; underneath outer bark, close to N199D and N187B.

*Leaf description*.—Appearance and arrangement: Flattened and closely appressed, scale-like; opposite, simple; sessile. Length: About 3 mm. Width: About 1.5 mm. Shape: Ovate. Apex: Acute. Base: Obtuse. Margin: Entire. Venation pattern: Parallel. Texture: Smooth, glabrous. Color: Developing leaves, upper and lower surfaces: Close to between 144A and 143A. Fully expanded leaves, upper surface, summer: Close to N137A. Fully expanded leaves, upper surface, winter: North-facing leaves: Close to between 139A and N137A. South-facing leaves: Close to 139A; distally close to 146A and at the apex, close to 164B. Fully expanded leaves, lower surface, summer: Close to 138A. Fully expanded leaves, lower surface, winter: North-facing leaves: Close to between 138A and 137B. South-facing leaves: Close to between 143B and 137B.

Cone description: To date, cone development has not been observed on trees of the new *Thuja*.

Landscape performance: To date, trees of the new *Thuja* have been observed to have good landscape performance, good winter hardiness and to tolerate temperatures ranging from about −14° C. to about 40.5° C.

Pathogen & pest resistance: To date, trees of the new *Thuja* have not been observed to be resistant to pathogens and pests common to *Thuja* trees.

It is claimed:

1. A new and distinct *Thuja* tree named 'Attapulgus' as illustrated and described.

* * * * *

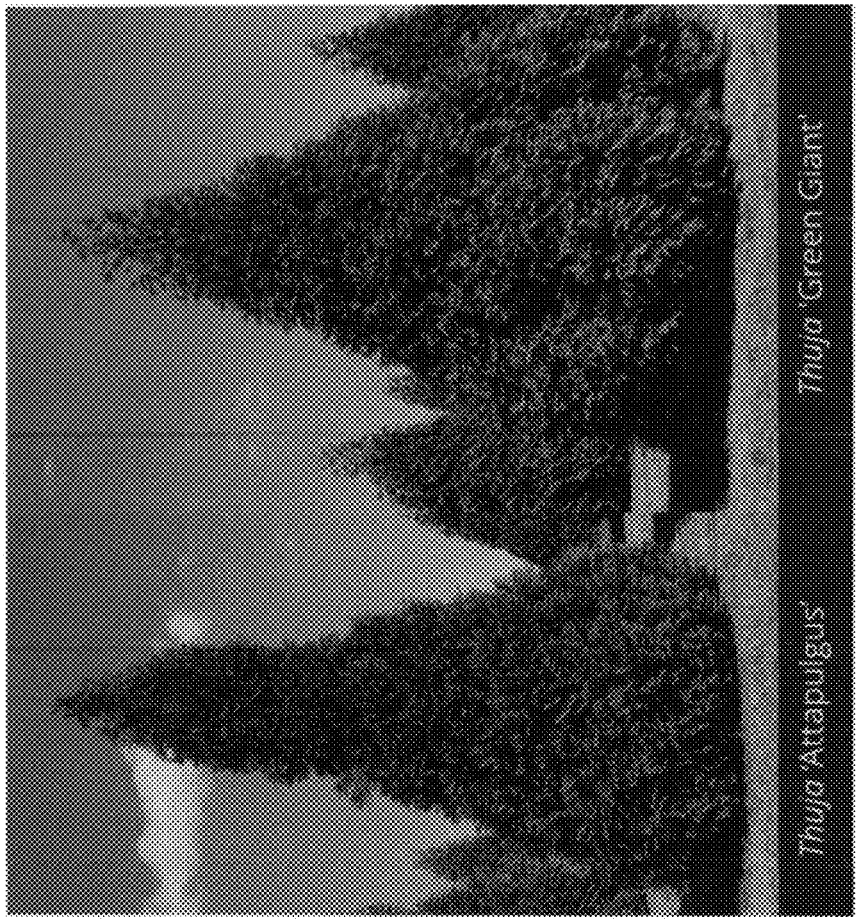
Thuja 'Green Giant'
Thuja Autepulgaris

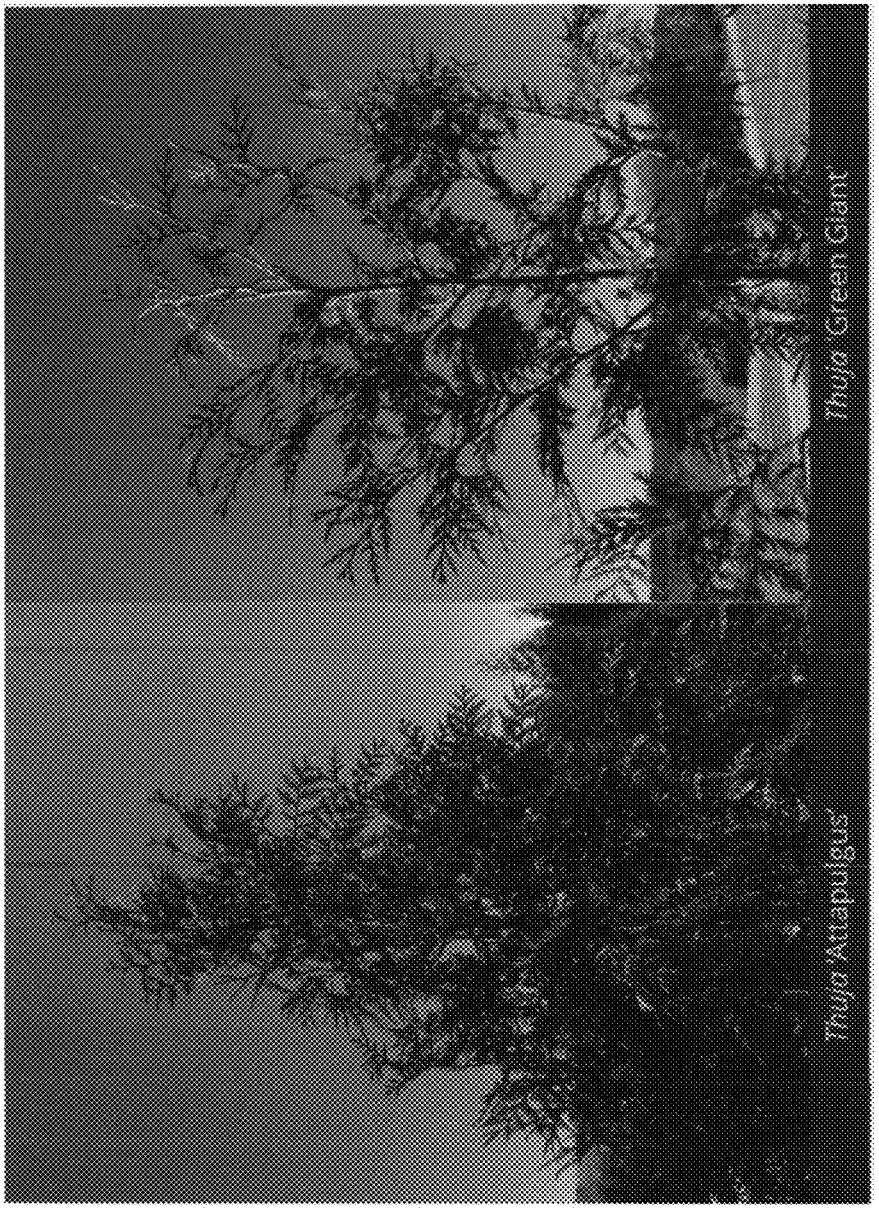
Thuja 'Green Giant'
Thuja 'Atropurpurea'

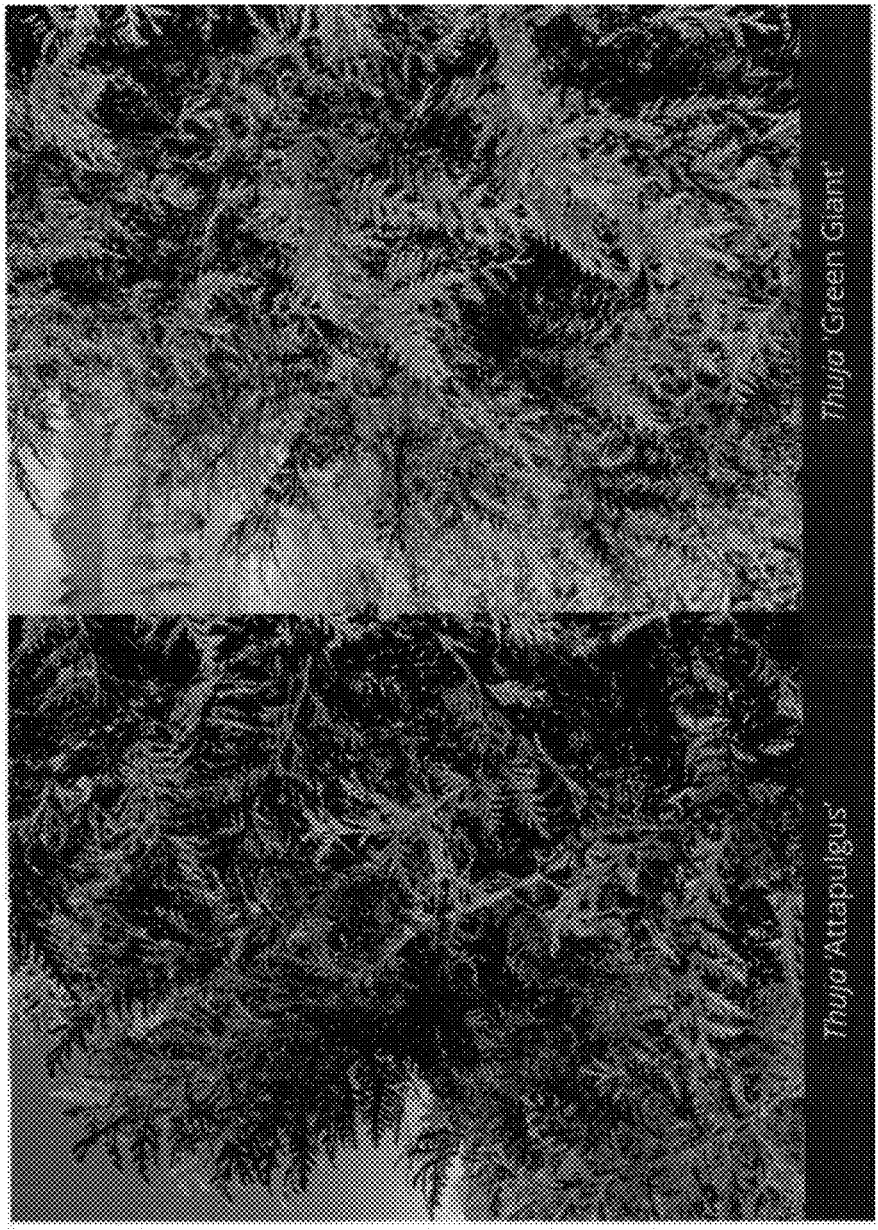
Thuja 'Green Giant'
Thuja Attenuatus

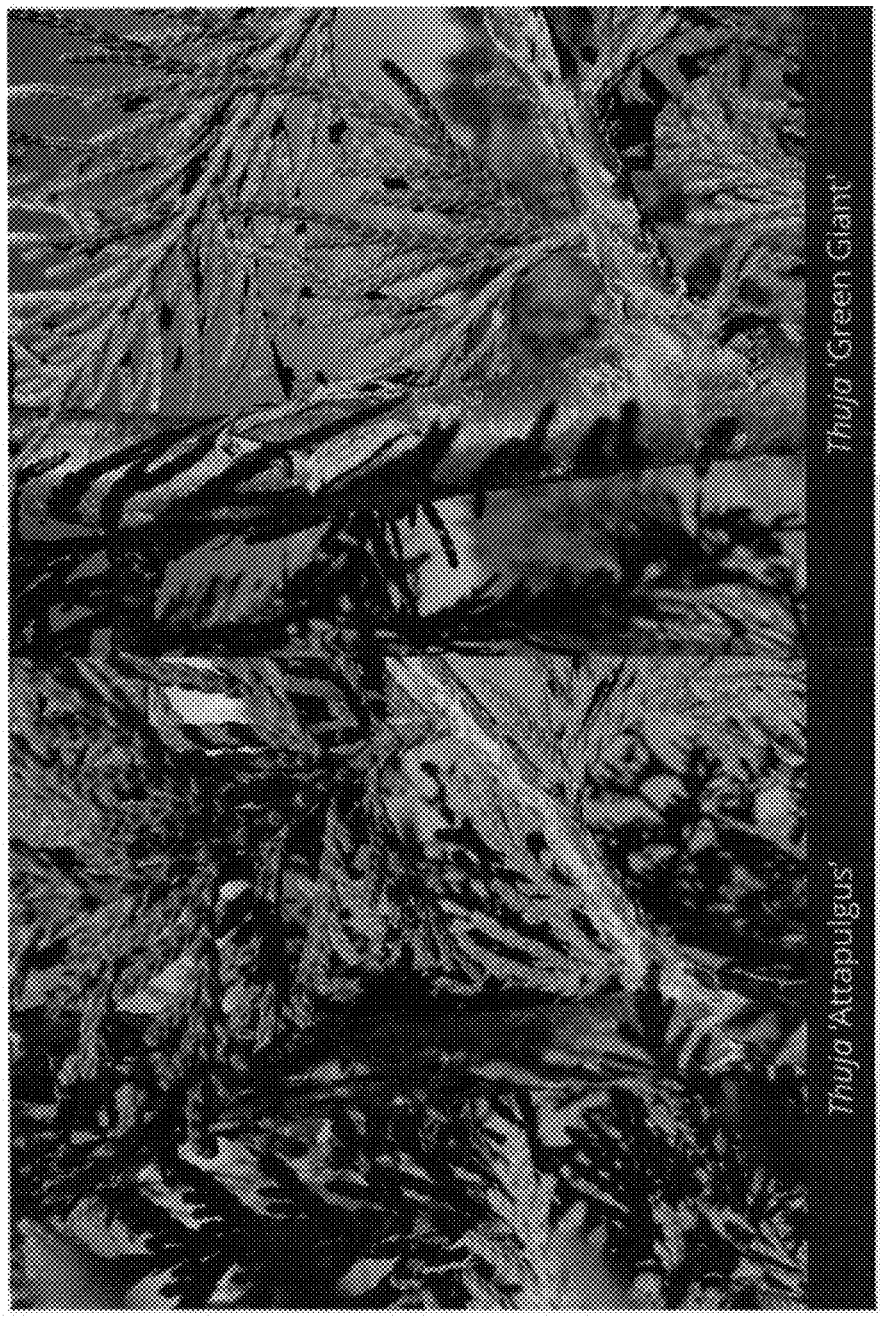
Imp/o Green Giant
Imp/o Attaunatus